US006877275B2

United States Patent
Glenn et al.

(10) Patent No.: US 6,877,275 B2
(45) Date of Patent: Apr. 12, 2005

(54) METHOD OF WEED CONTROL

(75) Inventors: David Michael Glenn, Shepherdstown, WV (US); Dennis G. Sekutowski, Stockton, NJ (US)

(73) Assignee: Engelhard Corporation, Iselin, NJ (US)

(*) Notice: Subject to any disclaimer, the term of this patent is extended or adjusted under 35 U.S.C. 154(b) by 35 days.

(21) Appl. No.: 10/078,628

(22) Filed: Feb. 19, 2002

(65) Prior Publication Data

US 2003/0159349 A1 Aug. 28, 2003

(51) Int. Cl.[7] .............................................. A01B 79/00
(52) U.S. Cl. ................................................ 47/58.1 SC
(58) Field of Search ................ 47/58.1 SC; 428/402.21

(56) References Cited

U.S. PATENT DOCUMENTS

| | | | | |
|---|---|---|---|---|
| 3,120,445 A | | 2/1964 | Aluisi et al. ................. 106/286 |
| 3,159,536 A | | 12/1964 | Marotta ........................ 167/12 |
| 3,287,103 A | * | 11/1966 | Sowa .......................... 504/191 |
| 3,455,673 A | * | 7/1969 | Goonewardene et al. ... 504/300 |
| 3,870,505 A | * | 3/1975 | Kaugars ....................... 504/343 |
| 4,071,374 A | | 1/1978 | Minton ........................ 106/189 |
| 4,098,600 A | | 7/1978 | Chupp .......................... 71/105 |
| 4,323,389 A | * | 4/1982 | Yoshimoto et al. ......... 504/352 |
| 4,382,868 A | | 5/1983 | House .......................... 252/28 |
| 4,828,835 A | * | 5/1989 | Meyers et al. .............. 424/409 |
| 5,106,410 A | * | 4/1992 | Puritch et al. ............... 504/142 |
| 5,190,764 A | * | 3/1993 | Chiba et al. ................. 424/408 |
| 5,783,520 A | * | 7/1998 | Anderson et al. ........... 504/140 |
| 6,156,327 A | * | 12/2000 | Sekutowski et al. ........ 424/405 |
| 2001/0031703 A1 | * | 10/2001 | Ueda .......................... 504/127 |

FOREIGN PATENT DOCUMENTS

| | | | | |
|---|---|---|---|---|
| JP | 2000060321 A | * | 2/2000 | .......... A01G/13/00 |
| SU | 375052 A | * | 3/1973 | ............ A01G/1/00 |
| WO | 9409626 | | 5/1994 | .......... A01N/25/04 |
| WO | WO 9838848 A1 | * | 9/1998 | ............ A01G/7/00 |

OTHER PUBLICATIONS

M. Bar–Joseph, H. Frenkel "Spraying Citrus Plants with Kaolin Suspensions Reduces Colonization by The Spiraea Aphid," Crop Prot 2 371–374 (1983).

* cited by examiner

Primary Examiner—Charles T. Jordan
Assistant Examiner—Francis T. Palo
(74) Attorney, Agent, or Firm—Melanie L. Brown; Amin & Turocy, LLP

(57) ABSTRACT

Disclosed are methods of reducing weed growth or reducing pests involving applying to plant producing media particulate materials to a depth of at least about 1 cm, wherein the plant producing media to the depth comprises about 1% by weight or more and about 25% by weight or less of the applied particulate materials Also disclosed are methods of reducing weed growth involving applying to plant producing media or unwanted vegetation a film of particulate materials, wherein the film has a thickness of about 1 μm or more and about 5 mm or less.

36 Claims, 1 Drawing Sheet

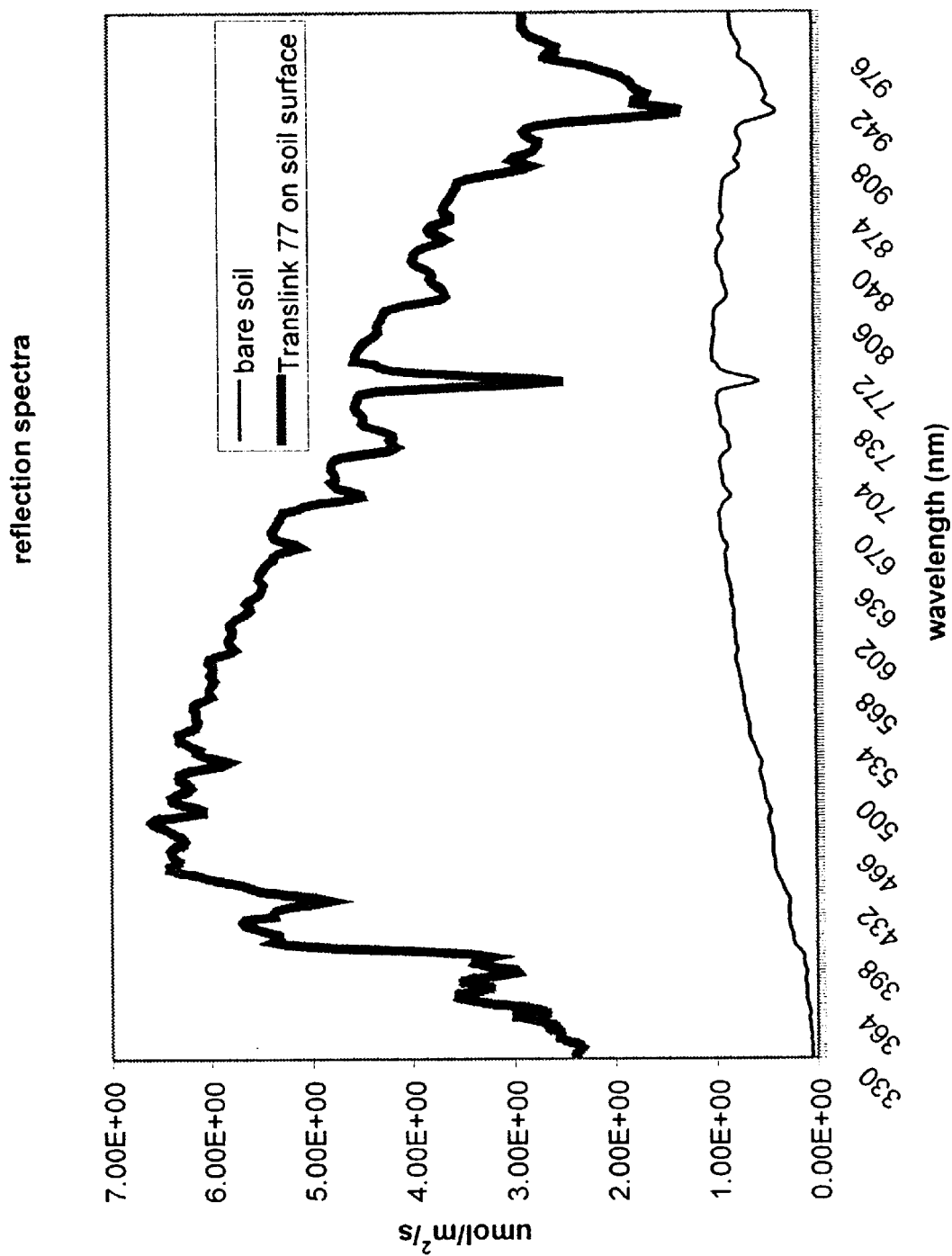

METHOD OF WEED CONTROL

TECHNICAL FIELD

The present invention is directed to soil or vegetation treated with a particulate film and methods for controlling unwanted vegetation either originating in the soil or immigrating to the site.

BACKGROUND OF THE INVENTION

The use of herbicidal chemicals and microbial agents to control unwanted vegetation, such as weeds, is known. For example, Wenger, U.S. Pat. No. 5,599,771 relates to an active ingredient of a pre-emergent and post-emergent herbicide, Harris and Stahlman U.S. Pat. No. 5,332,673 is a soil borne bacteria that controls downy brome, a weed problem in wheat production. Physical methods of weed control are also known. For example, Lahalih, et al U.S. Pat. No. 4,686,790 relates to preparing a mulch film from water soluble polymers and a water resistant resin. The mulch may contain nutrients or other additives. Monroe et al U.S. Pat. No. 5,532,298 relates to preparing a degradable agricultural ground cover composed of polyethylene polymer fiber and cellulose pulp that persists 8–12 weeks. Adamoli et al U.S. Pat. No. 5,674,806 relates to preparing aggregates from recycled paper for weed control. Christians U.S. Pat. No. 5,030,268 relates to preparing a mulch of corn gluten meal as a pre-emergent weed control material. The application of plastic mulch of various colors, compositions, and thicknesses is a common weed control practice. Oils of various sources are used in herbicide formulations. Low boiling oils, unsaturated oils and aromatic compounds in oils, themselves, can be herbicidal when applied to foliage (Gauvrit and Cabanne (1993) Pesticide Science 37:147–153, Oils for weed control: uses and mode of action). Reflective mulches increase light reflection into the canopy of plants, increasing photosynthesis and improving fruit color (Decoteau, E. R., M. J. Kasperbauer, and P. G. Hunt. 1989). Mulch surface color affects yield of fresh-market tomatoes (J. Amer. Soc. Hort. Sci. 114(2):216–219). Plastic mulches, while reducing weed growth also reduce disease and insect damage (T. K. Wolfenbarger, D. O. and W. D. Moore, 1968). Insect abundances on tomatoes and squash mulched with aluminum and plastic sheetings has been investigated (J. Econ. Entomol. 61(1):34–36 and Hartz, J. E. DeVay and C. L. Elmore, 1993). Solarization is an effective soil disinfestation technique for strawberry production (HortScience 28(2):104–106).

SUMMARY OF THE INVENTION

The present invention provides for weed control, enhanced horticultural effects, disease control, improved fruit yield, and pest (insect) control using particulate materials. The particulate materials can be applied as dust, in a slurry with water, or in an emulsion with water and a high boiling organic liquid.

Specifically in one embodiment, the present invention relates to methods of reducing weed growth or reducing pests involving applying to plant producing media particulate materials. The present invention also relates to land or plant producing media treated in accordance with these methods.

In another embodiment, the present invention relates to methods of reducing weed growth involving applying to plant producing media or unwanted vegetation a film of particulate materials. Alternatively, methods involve applying to unwanted vegetation an emulsion comprising water, particulate materials and a high boiling organic liquid to form a film. The present invention also relates to land, plant producing media or unwanted vegetation treated in accordance with these methods.

In yet another embodiment, the present invention relates to methods of increasing the size of fruit harvested from a fruit tree by applying an emulsion of water, particulate materials and a high boiling organic liquid so that a portion but not all of the flowers/blossoms abort.

BRIEF DESCRIPTION OF THE DRAWINGS

FIG. 1 is a reflectance spectrum of untreated soil and soil treated in accordance with the present invention.

DETAILED DESCRIPTION OF THE INVENTION

The present invention provides for weed control, enhanced horticultural effects, disease control, and pest control effects involving treating a substrate with a particulate material. Weed control or reducing weed growth involves preventing the weed from growing, partially killing the weed, killing the weed, and preventing a weed seed from germinating. The particulate material is applied to a substrate in any suitable manner, such as in the form of a dust or slurry.

Substrates that may be treated in accordance with the present invention generally include the unwanted vegetation, and plant producing media such as soil, organic materials such as peat and compost, inorganic substrates such as vermiculite, rockwool and other synthetic, inert growing media. Unwanted vegetation includes weeds, non-agricultural plants in the vicinity of agricultural crops, and other non-useful, non-ornamental plants. Specific examples of substrates include naturally occurring soils, amended soils, artificial media used to produce plants, weeds (the weed itself, roots of weeds, seeds of weeds, etc.), and the like.

Examples of unwanted vegetation include American beauty berry flower; American holly; angelica, purple-stemmed; annual sowthistle; aster; barnyardgrass; beggarsticks, (aka bur-marigold, sticktight); bergamot (horse-mint); big bluestem; bigroot morningglory (aka wild sweet potato); birdsfoot trefoil; bitter nightshade; black henbane; black (honey) locust (aka coffee bean tree); black medic; black nightshade; blackgrass; blue vervain; bouncingbet, (aka soapwort); brackenfern western (aka fiddlehead); bristly foxtail (aka bur bristlegrass); broadleaf dock; broadleaf plantain; browneyed susan (aka black-eyed susan); broomrape; crenate (aka scalloped broomrape); Egyptian broomrape; buckwheat; bull thistle; bur cucumber; burdock; buttercup; Canada thistle; cardinal flower (aka scarlet lobelia); carpetweed; castorbean; catchweed bedstraw; catnip; cattail; cheat; chickweed, common; chickweed, mouseear; chicory; Chinese lantern; chokecherry; cinquefoil; clammy; coundcherry; climbing milkweed, (aka honeyvine milkweed); cogongrass; common buttercup; common cocklebur; common lambsquarters; common mallow, (aka wild geranium, roundleaf mallow); common milkweed; common mullien (aka candelwick); common ragweed; common yarrow; compass plant; coneflower (purple); corn cockle; corn row; cornflower; cow cockle; creeping charlie; cupplant; curly dock (aka sour dock); cutleaf coneflower; daisy fleabane; dandelion; dodder, field (aka foddergrass); downy brome, (aka cheatgrass); eastern black shade; English ivy; evening primrose; fall panicum; fescue; field bindweed, (aka wild morningglory); field pennycress; flixweed; foxglove; foxtail barley; giant foxtail; giant green foxtail; giant ragweed, (aka horseweed); goatsbeard, (aka western salsify); goldenrod; goosegrass; goutweed; grain amaranth; ground cherry; ground ivy; hairy crabgrass; hedge bindweed; hemp, (aka marijuana); hemp dogbane, (aka Indian hemp); hemp sesbania (aka indigoweed); henbit; honeyvine milkweed, (aka climbing milkweed); hophornbeam copperleaf; horsenettle; horseweed (marestail); hyacinth; Indiangrass; ivy; ivyleaf morningglory; Jerusalem artichoke; jimsonweed; johnsongrass; knapweed; knotweed; kochia; ladysthumb smartweed; lambsquarter; longspine sandbur; maximillian sunflower; meadow foxtail; meadow salsify; morningglory; motherwort; mowed hay; musk thistle; narcissus; nettle; Ohio buckeye; orchardgrass; oxalis; palouse tarweed; Pennslyvania smartweed; Pennycress; perennial sowthistle; philodendron; phlox; pigweed; pigweed; pineappleweed; poison hemlock; poison ivy; pokeweed, common; poppy; prairie bush clover; prairie dock; prickly lettuce; prickly sida; prostrate spurge; purple coneflower; purple loosestrife; purslane; purslane speedwell; quackgrass; Queen Anne's lace; rattlebox; rattlesnake brome; red clover; redroot pigweed; redstem filaree; redtop; reed canarygrass; rough fleabane; roundleaf mallow; rush; Russian knapweed; salsify; scouring-rush, common; Scotch thistle; senicio; shattercane/wild cane; shepherdspurse; small whorled pogonia; smallflower buttercup; smartweed, light (or pale); smartweed, swamp; smooth bromegrass; smooth crabgrass; smooth groundcherry; sorghum almum; sowthistle; spiny amaranth; splitleaf philodendron; spotted knapweed; squirreltail; star of Bethlehem; stinging nettle; switchgrass; tall/ivyleaf morningglory; tall morningglory; tall waterhemp; tansy mustard, (aka pinole); thistles; tickseed coreopsis; Timothy trumpet creeper; velvetleaf, (aka elephant ear, butterprint); Venice mallow, (aka flower-of-an-hour); vetch; Virginia creeper; Virginia pepperweed; volunteer corn; *zea mays*; water hemlock; water-lilly; waterpod; white bryony on hawthorn; white clover; white snakeroot; white sweetclover; whorled milkweed; whorled tickseed; wild buckwheat; wild 4 o'clock; wild garlic; wild grape; wild mustard; wild onion; wild parsnip; wild proso millet; wild salsify; wild sunflower; wild sweet potato, (aka bigroot morningglory); wild violets; wirestem muhley; witchgrass; wood sorrel; woodland sunflower; woolly cupgrass; yarrow; yellow clover; yellow foxtail; yellow nutsedge, (aka chufa); yellow rocket; yew; yucca; and yellow nutsedge.

Pests range from bacteria to arthropods to microbes to mammals. For example, pests include bacteria, fungus, worms including nematodes, insects, arachnids such as spiders and mites, birds, rodents, deer, and rabbit. Substrates that may be treated in accordance with the present invention decrease or discourage the presence of pests in areas so treated.

The plants that benefit (growth is enhanced) as a result of the present invention include horticultural crops and especially agricultural crops and ornamental crops and seeds of agricultural crops and ornamental crops. The plants include actively growing agricultural crops, actively growing ornamental crops, fruiting agricultural crops and fruiting ornamental crops and the products thereof. Agricultural crops are plants used to make useful products, such as food products, feed products, fiber products and the like. Ornamental crops are plants used for decoration or aesthetic reasons. Examples include fruits, vegetables, trees, flowers, grasses, and landscape plants and ornamental plants. Specific examples include apple trees, pear treas, peach trees, plum trees, lemon trees, grapefruit trees, avocado trees, orange trees, apricot trees, walnut trees, raspberry plants, strawberry plants, blueberry plants, blackberry plants, bosenberry plants, corn, beans including soybeans, squash, tobacco, roses, violets, tulips, tomato plants, grape vines, pepper plants, wheat, barley, oats, rye, triticale, and hops. These plants are not unwanted vegetation. In most instances, these plants are not treated in accordance with the present invention.

The particulate materials suitable for use in the present invention are hydrophobic or hydrophilic. In one embodiment, the particulate materials are hydrophobic in and of themselves, (for example, mineral talc). In another embodiment, the particulate materials are hydrophilic materials that are rendered hydrophobic by application of an outer coating of a suitable hydrophobic wetting agent or coupling agent (for example, in an embodiment where a particulate material has a hydrophilic core and a hydrophobic outer surface). In yet another embodiment, the particulate materials are hydrophilic in and of themselves (calcined kaolins).

Examples of particulate hydrophilic materials suitable for use in the present invention include minerals, such as calcium carbonate, talc, kaolin (both hydrous kaolins and calcined kaolin), beneficiated kaolin, bentonites, clays, pyrophyllite, silica, feldspar, sand, quartz, chalk, limestone, precipitated calcium carbonate, diatomaceous earth and barytes; functional fillers such as aluminum trihydrate, pyrogenic silica, and titanium dioxide. Examples of non-mineral hydrophilic particles include carbon soot, coal dust, ash waste and other dark colored organic materials.

In one embodiment, the particulate materials suitable for use in the present invention are heat treated particulate materials. For purposes of this invention, heat treated particulate materials are particulate materials that have been heated to an elevated temperature and include baked particulate materials, calcined particulate materials, and fired particulate materials. Heat treated particulate materials are generally hydrophilic. Specific examples include calcined calcium carbonate, calcined talc, calcined kaolin, baked kaolin, fired kaolin, hydrophobic treated heat treated kaolin, calcined bentonites, calcined clays, calcined pyrophyllite, calcined silica, calcined feldspar, calcined sand, calcined quartz, calcined chalk, calcined limestone, calcined precipitated calcium carbonate, baked calcium carbonate, calcined diatomaceous earth, calcined barytes, calcined aluminum trihydrate, calcined pyrogenic silica, and calcined titanium dioxide.

Heat treatment in accordance with the invention involves heating a particulate material at a temperature from about 300° C. to about 1,200° C. for about 10 seconds to about 24 hours. In another embodiment, heat treatment involves heating a particulate material at a temperature from about 400° C. to about 1,100° C. for about 1 minute to about 15 hours. In yet another embodiment, heat treatment involves heating a particulate material at a temperature from about 500° C. to about 1,000° C. for about 10 minutes to about 10 hours. The heat treatment may be carried out in air, in an inert atmosphere or under a vacuum.

In these embodiments, the particulate materials contain at least about 25% by weight, and particularly about 25% to about 100% by weight of heat treated particulate materials. In another embodiment, the particulate materials contain at least about 40% by weight, and particularly about 40% to about 99% by weight of heat treated particulate materials.

The surfaces of the particulate hydrophilic materials can be made hydrophobic by contact with at least one hydrophobic wetting agent and/or coupling agent. Industrial mineral applications, especially in organic systems such as plastic composites, films, organic coatings or rubbers, utilize hydrophobic surface treatments to render a mineral surface hydrophobic; see, for example, Jesse Edenbaum, *Plastics Additives and Modifiers Handbook*, Van Nostrand Reinhold, New York, 1992, pages 497–500 which is incorporated herein by reference for teachings of such hydrophobic surface treatment materials and their application.

Coupling agents such as fatty acids and silanes are commonly used to surface treat solid particles as fillers or additives targeted to these industries. Such hydrophobic agents are known in the art. Examples include organic titanates such as Tilcom® from Tioxide Chemicals; organic zirconate or aluminate coupling agents from Kenrich Petrochemical, Inc.; organofunctional silanes such as vinyltriethoxysilane, vinyl tris-(2-methoxyethoxy)silane, γ-methacryloxypropyltrimethoxysilane, β-(3,4-epoxycyclohexyl)ethyltrimethoxysilane, γ-glycidoxypropyltrimethoxysilane, γ-mercaptopropyltrimethoxysilane, γ-aminopropyltriethoxysilane, N-β-(aminoethyl)-γ-aminopropyltrimethoxysilane, and β-mercaptoethyltriethoxysilane, and others under the trade designation Silquest® from Witco or those under the trade designation Prosil® from PCR; modified silicone fluids such as the DM-Fluids obtained from Shin Etsu; and fatty acids such as double pressed stearic acid and triple pressed stearic acid and others under the trade designation Hystrene® or Industrene® from Witco Corporation or those under the trade designation Emersol® from Henkel Corporation. In a specific embodiment, stearic acid and stearate salts are particularly effective for rendering a particle surface hydrophobic.

Further specific examples of particulate materials include calcined kaolins under the trade designation Satintone® and siloxane treated calcined kaolins under the trade designation Translink® from Engelhard Corporation, Iselin, N.J.; calcium carbonate under the trade designations Atomite® and Supermite® from English China Clay and stearic acid treated ground calcium carbonates under the trade designations Supercoat® and Kotamite® from English China Clay.

The particulate materials suitable for use in the present invention are finely divided. The term finely divided when utilized herein means that the particulate materials have a median individual particle size (average diameter) below about 100 μm. In one embodiment, the particulate materials have a median individual particle size of about 10 μm or less. In another embodiment, the particulate materials have a median individual particle size of about 3 μm or less. In yet another embodiment, the particulate materials have a median individual particle size of about 1 μm or less.

Particle size and particle size distribution as used herein are measured with a Micromeritics Sedigraph 5100 Particle Size Analyzer. Measurements are recorded in deionized water for hydrophilic particles. Dispersions are prepared by weighing 4 grams of dry sample into a plastic beaker, adding dispersant and diluting to the 80 ml mark with deionized water. The slurries are then stirred and set in an ultrasonic bath for 290 seconds. Typically, for kaolin 0.5% tetrasodium pyrophosphate is used as a dispersant; with calcium carbonate 1.0% Calgon T is used. Typical densities for the various powders are programmed into the sedigraph, for example, 2.58 g/ml for kaolin. The sample cells are filled with the sample slurries and the X-rays are recorded and converted to particle size distribution curves by the Stokes equation. The median particle size is determined at the 50% level.

The particulate materials of the present invention are highly reflective. As used herein, highly reflective means a material having a "Block Brightness" of at least about 80, as measured by TAPPI standard T 646. In another embodiment, the Block Brightness of the particulate materials is at least about 90. In yet another embodiment, the Block Brightness of the particulate materials is at least about 95. Measurements can be made on a Reflectance Meter Technidyne S-4 Brightness Tester manufactured by Technidyne Corporation which is calibrated at intervals not greater than 60 days using brightness standards (paper tabs and opal glass standards) supplied by the Institute of Paper Science, or Technidyne Corporation. Typically a particle block or plaque is prepared from 12 grams of a dry (about less than 1% free moisture) power. The sample is loosely placed in a cylinder holder and a plunger is slowly lowered over the sample to a pressure from about 29.5 to about 30.5 psi and held for about 5 seconds. The pressure is released and the plaque is examined for defects. A total of three plaques are prepared and three brightness values are recorded on each plaque by rotating the plaque about 120 degrees between readings. The nine values are then averaged and reported.

The particulate materials particularly suitable for use in this invention are inert and nontoxic. As used herein, inert particulate materials are particles that are not phytotoxic to horticultural crops and ornamental crops. However, the unique combinations in or on soil and other plant producing substrates and unique combinations with other materials, are in some instances phytotoxic (generally to unwanted vegetation such as weeds). For example, seeds of crops may be planted in soil at a depth of 4" and the particulate materials are intermixed with soil to a depth of 3". In this example, the particulate materials are phytotoxic to weed seeds in the soil at a depth to 3", but not phytotoxic to the crop seeds planted at a depth of 4". Determining whether a given combination is phytotoxic can be performed by one skilled in the art. The particulate materials are preferably nontoxic meaning that, in the quantities needed for effective weed control, such materials are not considered harmful to animals, the environment, the applicator and the ultimate consumer, if any, of agricultural products made in connection with the present invention.

This invention relates to methods of weed control wherein the surface of the soil, unwanted vegetation, or a plant-producing substrate is treated with one or more particulate materials. In particular, a suitable amount of particulate materials are contacted with the surface of a substrate (surface of soil, unwanted vegetation, or plant-producing substrate).

In one embodiment, the entire surface of a substrate is covered with the particulate materials. Full substrate coverage tends to provide effective weed control, and disease and insect control. In another embodiment, less than the entire surface is covered with the particulate materials. In these embodiments, partial coverage is highly effective, for example, discontinuous coverage allows reflection of light and infrared radiation from the particulate materials while providing effective weed control. In another embodiment, the method of the present invention results in the formation of a membrane or film of one or more layers of highly reflective particulate materials on the soil surface, unwanted vegetation surface or the surface of other plant-producing substrates. The membrane or film may partially cover the substrate surface, substantially cover the substrate surface, or entirely cover the substrate surface. The film may be coherent or incoherent.

In one embodiment, the particulate materials are applied to a substrate as a slurry of finely divided particles in a volatile liquid such as water, a low boiling organic solvent or low boiling organic solvent/water mixtures. One or more layers of this slurry can be sprayed or otherwise applied to the substrate. Additives such as surfactants, dispersants, speaders/stickers (adhesives), low boiling organic liquids, high boiling organic liquids, salts, agrichemicals, and colored particles may be incorporated into the slurry of the particulate materials. Additives also include oils and non-volatile, high boiling organic materials. The particulate materials when applied as a slurry are hydrophobic particulate materials or hydrophilic particulate materials.

In another embodiment, the particulate materials are applied to a substrate as a dry dust and incorporated into the substrate (when the substrate is soil or other plant-producing surface). The resultant residue of this treatment may be hydrophilic or hydrophobic. The particulate materials when applied as a dry particles are hydrophobic particulate materials or hydrophilic particulate materials, but preferable hydrophobic particulate materials.

In yet another embodiment, the particulate materials are applied to a substrate as an emulsion of water, and a high boiling organic liquid. In this embodiment, the particulate materials are initially mixed with the high boiling organic liquid and then mixed with water to form a stable emulsion. Mixing of the particulate materials with the high boiling organic liquid can involve high shear mixing, in order to promote the formation of a stable emulsion after water is added. The particulate materials when applied as an emulsion are hydrophobic particulate materials or hydrophilic particulate materials, but preferable hydrophilic particulate materials.

Spreader/stickers that can be mixed with hydrophilic particles (for example, about 3% by weight or more solids in water) to aid in spraying uniform treatments on horticultural substrates are: modified phthalic glycerlol alkyd resins such as Latron B-1956 from Rohm & Haas Co.; plant oil based materials (cocodithalymide) with emulsifiers such as Sea-wet from Salsbury lab, Inc.; polymeric terpenes such as Pinene II from Drexel Chemical Co.; nonionic detergents (ethoxylated tall oil fatty acids) such as Toximul 859 and Ninex MT-600 series from Stephan.

In another embodiment, agrichemicals are incorporated into the particle slurry or particle-substrate mix. Examples of agrichemicals include nutrients, microbial agents, fertilizers, herbicides, pesticides, fungicides, insecticide, and the like.

In yet another embodiment, the particulate materials contain particles of various colors, so that when the particulate materials are applied to a substrate (soil, unwanted vegetation or a plant-producing substrate) the spectrum of reflected light or heat exchange from the substrate is altered. Such colored particles may non-reflective. Examples include natural iron oxides such as yellow limonite, red hematite, brown limonite; black iron oxides such as Pigment Black 10; synthetic iron oxides such as copperas red and ferrite red; precipitated red iron oxide; brown iron oxides such as Pigment Brown 6 and brown ocher; synthetic black iron oxides such as Pigment Black 1 and synthetic magnetite; copper-black; chrome-black; zinc magnesium ferrite pigments such as Pigment Brown 11 and mapioc tans; carbon black pigments such as Pigment Black 6 or 7, furnace black, channel black, acetylene black, furnace black, bone black and lampblack; graphite including natural and synthetic graphites such as electrographite or artificial graphite; aniline black such as Pigment Black 1; logwood black lakes such as Natural Black 3, Lake, Logwood Pigment; and the like.

The low boiling organic liquids preferably include water-miscible and organic solvents. In one embodiment, the low boiling organic liquids contain from 1 to about 6 carbon atoms. The term low boiling as used herein means organic liquids which have a boiling point generally no higher than about 100° C. These liquids promote the ability of the particulate materials to remain in a finely divided state without significant agglomeration. Examples of low boiling organic liquids include alcohols such as methanol, ethanol, propanol, i-propanol, butanol, i-butanol, and the like, glycols (polyols), ketones such as acetone, methyl ethyl ketone and the like, and cyclic ethers such as ethylene oxide, propylene oxide and tetrahydrofuran. Combinations of the above-mentioned low boiling organic liquids, with or without water, can also be employed. Methanol is a preferred low boiling organic liquid.

Low boiling organic liquids may be employed to facilitate applying the particulate materials by spraying to substrates. Typically, the low boiling organic liquids are used in an amount sufficient to facilitate the formation a dispersion of the particulate material. In one embodiment, the amount of low boiling organic liquid is up to about 30% (volume percent) of the dispersion. In another embodiment, the amount of low boiling organic liquid is from about 1% to about 20% (volume percent) of the dispersion. In yet another embodiment, the amount of low boiling organic liquid is from about 2% to about 10% (volume percent) of the dispersion. The particulate material is preferably added to a low boiling organic liquid to form a slurry and then this slurry is diluted with water to form an aqueous dispersion.

High boiling organic liquids including oils and fatty acids may be employed in applying the particles to substrates for the purposes of this invention. The term high boiling as used herein means organic liquids which have a boiling point generally higher than about 100° C. Typically, the high boiling organic liquids and/or oils are used in an amount sufficient to facilitate the formation of a emulsion of the particulate material. In one embodiment, the amount of high boiling organic liquid is up to about 30% (volume percent) of the emulsion. In another embodiment, the amount of high boiling organic liquid is from about 1% to about 20% (volume percent) of the emulsion. In yet another embodiment, the amount of high boiling organic liquid is from about 2% to about 10% (volume percent) of the emulsion. The particulate material is added to a high boiling organic liquid and/or oil to form a slurry, or the particulate material is added to a high boiling organic liquid and/or oil with water to form an emulsion-slurry.

Examples of high boiling organic liquids include vegetable, industrial, marine, and paraffin oils including cottonseed oil, palm oil, peanut oil, corn oil soya oil, castor oil, linseed oil, rapseed oil, tung oil, oiticica oil, fish oil, sperm oil, Menhaden oil, and the like. Further examples of high boiling organic liquids include fatty acids such as saturated and unsaturated fatty acids including C6 to C32 carboxylic acids. Specific examples include caproic acid, caprrylic acid, pelargonic acid, capric acid, lauric acid, myristic acid, pentadecyclic acid, palmitic acid, margigaric acid, strearic acid, lauroleic acid, myristoleic acid, palmitoleic acid, oleic acid, linoleic acid, linolenic acid, and the like. Commercially available oils include Orchex® products from Exxon, Volck oils from Chevron, Pennzspray® products from Pennzoil-Quaker State, and Sunspray® products from Sunoco.

In another embodiment, salts are incorporated into the particle slurry or particle-substrate mix. Additive salts include ionic salts such as sodium chloride, potassium chloride, calcium chloride, magnesium chloride, sodium sulfate, potassium sulfate, calcium sulfate, magnesium sulfate, sodium nitrate, potassium nitrate, calcium nitrate, magnesium nitrate, sodium carbonate, potassium carbonate, magnesium carbonate, sodium nitrite, and potassium nitrite.

Several high boiling organic liquids are particularly effective at increasing the phytotoxicity of the particulate compositions thereby further enhancing the weed control abilities. In this connection, in one embodiment, the high boiling organic liquids include those with about 9 or more carbon atoms and about 20 or less carbon atoms; those with an odd number of carbon atoms; and those with unsaturation or aromaticity.

The resulting slurry or emulsion retains the particles in finely divided form or as agglomerates wherein most of the particulate materials are dispersed to a particle size of less than about 100 microns, regardless of whether a high boiling organic liquid, low boiling organic liquid, or a high boiling organic liquid and low boiling organic liquid are employed. In one embodiment, 90% by weight or more of the particulate materials have a particle size of less than about 10 microns. In another embodiment, 90% by weight or more of the particulate materials have a particle size of less than about 3 microns. In yet another embodiment, 90% by weight or more of the particulate materials have a particle size of less than about 1 micron.

When agglomerates are formed, the slurry or emulsion contains 90% by weight or more of the particulate materials having an agglomerate size of less than about 500 microns. In another embodiment, the slurry or emulsion contains 90% by weight or more of the particulate materials having an agglomerate size of less than about 250 microns.

The particle treatment may be applied as one or more layers of finely divided particulate material. The amount of material applied varies depending upon a number of factors, such as the identity of the substrate and the identity of the particulate material, etc. In any given instance, the amount of material applied can be determined by one of ordinary skill in the art. The amount may be sufficient to form a continuous film or intermittent film over all or a portion of the soil or other plant-producing substrate to which the particle treatment is applied. In one embodiment, the particle treatment is particularly effective when the surface is white in appearance, or the desired color in appearance.

In one embodiment, from about 1% to about 99% by weight of particulate material is applied in the substrate when incorporated into a substrate (for example, a mixture of particulate material and soil is applied to soil). In another embodiment, from about 5% to about 80% by weight of particulate material is applied into a substrate when incorporated into the substrate (such as soil or a plant-producing substrate).

In one embodiment, from about 5% to about 50% by weight of particulate material is applied as a slurry to a substrate (for example, a mixture of particulate material and liquid to the surface of unwanted vegetation). In another embodiment, from about 20% to about 40% by weight of particulate material is applied as a slurry to the surface of a substrate. The treated substrate may then be tilled to intermix the particulate material in the substrate.

Whether applied as a dust, mixed with substrate (such as soil) and applied, mixed in a slurry (aqueous and or organic liquid) and applied, particulate materials are applied to a substrate in an amount sufficient to at least one of reduce unwanted vegetation, reduce the presence or undesirable effects of pests, reduce disease, and enhance horticultural effects of crops or other wanted vegetation. Generally speaking, the particulate materials are applied, wet or dry, to become intermixed with a substrate or to coat a substrate. Intermixing may be accomplished by turning or roto-tilling the soil treated with the particulate materials.

Generally, the particulate materials are applied to a substrate in any suitable manner. For example, the particulate materials may be applied to a substrate by contacting a slurry comprising the particulate materials with the plant producing media or unwanted vegetation. When a film is formed over a plant producing media, the film may act as a pre-emergent herbicide. Alternatively, the particulate materials may be applied to a substrate in powder form and optionally mixing the particulate materials with the substrate when the substrate is a plant producing media. In another embodiment, the particulate materials may be applied to a substrate by mixing the particulate materials with loose plant producing media (typically soil) to form a mixture, and applying the mixture to the substrate, typically plant producing media.

In embodiments where the particulate materials become intermixed with a substrate, such as mixed with soil or other plant producing media, the depth of the intermixing is at least about 1 cm from the surface. In another embodiment, the depth of the intermixing is at least about 3 cm down to about 30 cm from the surface. In yet another embodiment, the depth of the intermixing is at least about 5 cm to about 20 cm from the surface. When mixed with the plant producing media, the particulate materials can be substantially uniformly mixed therein, or they can be randomly dispersed therein.

In one embodiment, in the intermixed growing medium, the amount of particulate materials is about 1% by weight or more and about 25% by weight or less. In another embodiment, in the intermixed growing medium, the amount of particulate materials is about 2% by weight or more and about 15% by weight or less. In yet another embodiment, in the intermixed growing medium, the amount of particulate materials is about 3% by weight or more and about 10% by weight or less.

In addition to being intermixed to a certain depth from the surface, the particulate materials may be intermixed in a discrete layer below the surface of the planting medium. For example, the particulate materials may be intermixed in a 7 cm thick layer located 5 cm below the surface (from 5 cm to 12 cm below the surface).

In embodiments where the particulate materials coat a substrate, the particulate materials form a coating or film, continuous or intermittent, over the growing medium or unwanted vegetation. In one embodiment, where continuous or present, the coating has a thickness of about 1 $\mu$m or more and about 5 mm or less. In another embodiment, the coating has a thickness of about 5 $\mu$m or more and about 2 mm or less.

In some instances, environmental conditions such as wind and rain may reduce the coverage (residue) of the particulate materials and therefore it is desirable to apply the particles one or more times during the growing season in order to maintain the desired effect of invention.

In one embodiment, the particulate films made in accordance with the present invention do not materially affect the exchange of gases on the surface of said soil. The gases which pass through the particle treatment (or residue from the inventive treatment) are those which are typically exchanged through the soil or plant-producing substrates. Such gases include water vapor, carbon dioxide, oxygen, nitrogen and volatile organics.

In another embodiment, the particulate materials may form a gas impermeable film that restricts the exchange of gases on the surface of the soil, a plant-producing substrate and/or unwanted vegetation. In this embodiment, a gas impermeable film trapping gases in the soil is formed. The gases which do not pass through the particle treatment of this embodiment are those which are typically exchanged through the substrates. Such gases include water vapor, carbon dioxide, oxygen, nitrogen and volatile organics and applied agrichemicals such as fumigants.

The particulate materials may be used in methods for weed control, methods for enhanced horticultural effects, methods for disease control, and methods for pest control effects. Weed control involves at least one of inhibiting the growth of existing weeds, preventing the growth of new weeds, and terminating the life of existing weeds. Enhanced horticultural effects include at least one of increasing the growth rate of agricultural and/or ornamental crops, increasing the health of agricultural and/or ornamental crops, increasing the life span of agricultural and/or ornamental crops, increasing the amount of fruit or flowers produced by agricultural and/or ornamental crops, and strengthening the root systems of agricultural and/or ornamental crops. Disease control involves at least one of decreasing the incidence of viral diseases in agricultural and/or ornamental crops, bacterial diseases, fungal diseases, and insect spread diseases. Pest control is one of decreasing the damage of agricultural and/or ornamental crops to insect, arachnid and/or nematode infestation, decreasing insect, arachnid and/or nematode infestation of soil or growth media of agricultural and/or ornamental crops, preventing insect, arachnid and/or nematode infestation of soil or growth media of agricultural and/or ornamental crops, and preventing insect, arachnid and/or nematode infestation of agricultural and/or ornamental crops.

When it is no longer desired to continue practicing the inventive method of weed control, the treated substrates are incorporated and dispersed (mixed) into the soil or other plant-producing substrate by conventional tillage practices to disrupt the treatment initially applied to the substrate.

The particulate materials may be also used in methods for thinning the number of flowers on a fruit tree, typically in bloom, so that the fruit that forms on a given branch does not have to compete with an adjacent fruit for tree nutrients. In this particular embodiment, an emulsion containing water, the particulate materials and one or more high boiling organic solvents are applied to a fruit tree. The application causes a number of the blossoms/flowers to abort, but not all of the blossoms/flowers. This typically happens within about 2 weeks after application, and in some instances, within about 1 week after application. As a result of the flower thinning, the fruit that is harvested from the treated fruit tree is larger and healthier than fruit harvested from a similar untreated fruit tree. Taste is also improved in the fruit that is harvested from the treated fruit trees.

In one embodiment, the application of a particulate material emulsion aborts at least about 25% (by number) of the blossoms/flowers of the fruit tree, and the fruit harvested therefrom is about 5% by weight or more larger than fruit from an untreated tree. In another embodiment, the application of a particulate material emulsion aborts at least about 50% (by number) of the blossoms/flowers of the fruit tree, and the fruit harvested therefrom is about 10% by weight or more larger than fruit from an untreated tree. In yet another embodiment, the application of a particulate material emulsion aborts at least about 60% (by number) of the blossoms/flowers of the fruit tree, and the fruit harvested therefrom is about 15% by weight or more larger than fruit from an untreated tree.

The following examples illustrate the present invention. Unless otherwise indicated in the following examples, in the specification and in the appended claims, all parts and percentages are by weight, temperatures are in degrees centigrade and pressures are at or near atmospheric pressure.

EXAMPLE 1

A water release curve is determined for soil amended with increasing amounts of Translink® 77, a hydrophobic material. A pressure membrane apparatus (Soil Moisture Eqpt. Santa Barbara, Calif., model 1600) with a 5 bar air entry value is used. Soil rings (48 mm diameter and 10 mm height) are filled with soil (Hagerstown silt loam) and varying amounts of Translink® 77 (0, 1, 2, 3, 4% by weight of soil). The rings and soil are placed in standing water for 30 days and then subjected to pressure differentials (−0.05, −0.1, −0.5, −1, −2, −3 atmospheres) on the membrane plate to simulate known levels of soil drying. Pressure differentials in the range of −0.05 to −0.5 atmospheres represent well water soil, while pressure differentials in the range of −2 to −3 atmospheres represent dry soils that do not easily support plant growth.

Effect of pressure differential and hydrophobic particle additions on volumetric soil water content (volume water/volume soil) is shown in Table 1.

TABLE 1

| % Translink ® 77 | Pressure differential or soil moisture tension (-atmospheres) | | | | | |
|---|---|---|---|---|---|---|
| to soil (w/w) | 0.05 | 0.1 | 0.5 | 1 | 2 | 3 |
| 0 | 0.49 | 0.38 | 0.31 | 0.24 | 0.17 | 0.15 |
| 1 | 0.38 | 0.31 | 0.27 | 0.18 | 0.16 | 0.14 |
| 2 | 0.37 | 0.29 | 0.26 | 0.19 | 0.18 | 0.15 |
| 3 | 0.30 | 0.26 | 0.24 | 0.15 | 0.13 | 0.15 |
| 4 | 0.25 | 0.25 | 0.23 | 0.14 | 0.14 | 0.14 |

Decreasing the pressure differential or soil moisture tension, i.e. more negative, dries the soil and decreases the water content of the soil. The addition of hydrophobic particles in increasing amounts at a specified soil moisture tension further reduces the water content of the soil in the range of −0.05 to −2 atmospheres. Therefore the addition of hydrophobic particles makes water less available, particularly in the well-watered range of −0.05 to −0.5 atmospheres.

EXAMPLE 2

Weed seed from four species (barnyard grass, *Echinochloa crusgalli*, nutsedge, *Cyperus esculentus*, Canada thistle, *Cirsium arvense*, lambsquarter, *Chenopodium album*) and two crop species (wheat, *Triticum aestivum*, sorghum, Sorghum bicolor) are treated in 6 planting arrangements:

1. Plant on soil and cover with 1 cm of soil
2. Plant on soil and cover with 2 cm of soil
3. Plant on soil and cover with 1 cm of soil containing 5% (w/w) of Translink® 77

4. Plant on soil and cover with 2 cm of soil containing 5% (w/w) of Translink® 77
5. Plant on 1 cm thick layer of soil containing 5% (w/w) Translink® 77 which over lays soil and the seed are covered with 1 cm of soil containing 5% (w/w) Translink® 77
6. Plant on 1 cm thick layer of soil containing 5% (w/w) Translink® 77 which over lays soil and the seed are covered with 2 cm of soil containing 5% (w/w) Translink® 77

The soil is a Hagerstown silt loam that is screened to pass a 4 mm screen and is heat sterilized to kill endemic weed seed. Ten seeds of each species are planted in pots containing 5 cm of soil and the treatments are overlain on this soil. The pots are watered weekly by submerging the pots in a layer of water 2 cm deep for 1 to 2 hours. The surface of each pot is misted with water daily.

The study is arranged in a randomized block design with 3 replications. Seed are planted and harvested. At harvest the number of plants in each container and their weight on drying at 60° C. is measured.

The effect of amending soil with a hydrophobic particle Translink® 77 on seed germination and growth is shown in Table 2.

TABLE 2

| Plant species | | Seed position treatment | | | | | |
|---|---|---|---|---|---|---|---|
| | | 1 | 2 | 3 | 4 | 5 | 6 |
| Wheat | Weight g/pot | 6.8 | 5.4 | 4.4 | 4.3 | 0.7 | 0.8 |
| | tot # of plants | 48 | 47 | 47 | 44 | 12 | 4 |
| Barnyard grass | Weight g/pot | 3.7 | 4.6 | 8.3 | 5.0 | 0.1 | 0.0 |
| | tot # of plants | 19 | 18 | 22 | 17 | 1 | 0 |
| Nutsedge | Weight g/pot | 8.9 | 14 | 8.6 | 18.2 | 0 | 0 |
| | tot # of plants | 30 | 27 | 23 | 25 | 0 | 0 |
| Canada Thistle | Weight g/pot | 0.6 | 0.6 | 0.3 | 0.3 | 0 | 0 |
| | tot # of plants | 39 | 34 | 35 | 32 | 0 | 0 |
| Sorghum | Weight g/pot | 6.4 | 7.1 | 7.1 | 5.6 | 0 | 0 |
| | tot # of plants | 44 | 47 | 41 | 44 | 1 | 0 |
| Lambs-quarter | Weight g/pot | 1.4 | 1.9 | 0.3 | 0.4 | 0 | 0 |
| | tot # of plants | 33 | 28 | 23 | 27 | 0 | 0 |

The data indicate that when weed or crop seeds are planted or occur on soil and are covered with a soil amended with 5% Translink® 77, seed germination is not appreciably inhibited (treatments 1–4). However, if the weed seeds are incorporated into the Translink® 77 amended soil, seed germination is greatly reduced (treatments 5 and 6). Although not wishing to be bound by any theory, it is believed that the reduction in seed germination is due, in part, to the reduced availability of water in the amended soil as demonstrated in Table 1.

EXAMPLE 3

A site is in permanent pasture for 5 years prior to rototilling in early August. After rototilling, 1 m by 1 m plots of untreated soil and treated soil are established in a paired-t-test design with 6 replications on August 29, same year. The treated soil receives 1.2 kg/m2 of Translink® 77, a hydrophobic kaolin particle from Engelhard Corp. Translink® 77 is incorporated uniformly into the upper 3 cm of soil with hand cultivation. The concentration of Translink® 77 is approximately 3% by weight and 20% by volume in the 3 cm treated soil region. On May 6 of the following year, biomass samples from the center of each plot are clipped and weighed following drying at 60° C. A circular area of 1,195 cm$^2$ is sampled in the center of each plot. Dry mass of vegetation in the untreated treatment is 218.5 g/m$^2$ and is significantly higher (p=0.05) than the 23.5 g/m$^2$ harvested from the treated soil. The data demonstrate that when soil is amended with 3% hydrophobic particles, seed germination in the amended zone is greatly inhibited. Although not wishing to be bound by any theory, it is believed that the inhibition is due to the reduced availability of water in the amended zone for seed germination. The occurrence of some seed germination is likely due, in part, to seeds germinating at the amended soil-natural soil interface as demonstrated in Table 2.

EXAMPLE 4

Nutsedge seeds are planted 1 cm deep in pots with 5 cm of a Hagerstown silt loam. Pots receive 6 treatments:
1. nothing
2. cover with an airtight, waterproof covering of Parafilm
3. cover with a 5 mm covering of Translink® 77, a hydrophobic particle
4. cover with a 1 mm covering of cottonseed oil
5. cover with a 1 mm covering of 30% (w/v) of Translink® 77 in cottonseed oil
6. cover with a 1 mm covering of 30% (w/v) of Satintone® 5HB, a hydrophilic particle, in cottonseed oil The pots are submerged in 2 cm of water for 1 to 2 hours weekly. The study is a completely randomized design with 8 replications. The effect of mulch treatments on nutsedge growth (cm length of each shoot) is shown in Table 3.

TABLE 3

| Treatment | Length of shoot (cm) |
|---|---|
| Untreated control | 20.3 |
| Covered with Parafilm | 26.6 |
| Covered with 5 mm Translink ® 77 as a dry material | 16.5 |
| Covered with 1 mm of cottonseed oil (CSO) | 6.1 |
| Covered with 1 mm of 30% Translink ® 77 in CSO | 2.0 |
| Covered with 1 mm of 30% Satintone ® 5HB in CSO | 0 |

These data indicate that a mixture of either a hydrophobic or hydrophilic material together with cottonseed oil makes a barrier to seed germination that is more effective than either the dry material or cottonseed oil alone. This inhibition is not due to exclusion of air since the covering of Parafilm did not inhibit seed germination.

EXAMPLE 5

A reflectance spectrum of soil and soil treated with a hydrophobic material (Translink® 77) is measured under full sun conditions using a Licor 1800 spectrometer. The reflectance spectrum is shown in FIG. 1, wherein wavelength is plotted against $\mu$mol/m$^2$/s.

The data indicate that the amendment of soil with a white material increases the reflection of visible and infrared radiation.

EXAMPLE 6

Tomato (*Lycopersicon lycopersicon*) and bean (*Phaseolus vulgaris*) are treated with the following treatments:
1. no treatment
2. spray with cottonseed oil
3. spray with 30% Translink® 77 in cottonseed oil
4. spray with 30% Satintone® 5HB in cottonseed oil 5. dust with Translink® 77

6. dust with Satintone® 5HB

Seven days after application plants are evaluated as alive or dead. A randomized block design with 3 replications is used and the results are shown in Table 4.

TABLE 4

| Treatments | Plant condition/# plants |
| --- | --- |
| Untreated control | Alive/3 |
| Cottonseed oil spray (CSO) | Alive/3 |
| Translink ® 77 in CSO | Dead/3 |
| Satintone ® 5HB in CSO | Dead/3 |
| Translink ® 77 dusted | Alive/3 |
| Satintone ® 5HB dusted | Alive/3 |

These data indicate that the application of cottonseed oil or particles alone does not kill vegetation. However, the combination of cottonseed oil and hydrophobic (Translink® 77) or hydrophilic (Satintone® 5HB) particles does kill vegetation.

EXAMPLE 7

An 8 ft by 10 ft area beneath apple trees is treated with the following treatments:

1) an untreated control
2) 6 pounds of ASP 672 (hydrous kaolin), 0.6 gal cottonseed oil, and 4.4 gal water are combined by mixing the kaolin and oil together and then adding the mixture to water and gently agitating
3) 6 pounds of ASP 672 (hydrous kaolin), 0.6 gal cottonseed oil, 0.15 lbs of iron oxide, and 4.4 gal water are combined by mixing the kaolin, iron oxide and oil together and then adding the mixture to water and gently agitating.

Treatments 2) and 3) are applied at the rate of 50 gallons of solution/acre or 11.75 oz/plot or 350 ml/plot. Nothing is applied to the untreated control. Applications are made April 27, May 31 and July 5. The cottonseed oil does not contain any emulsifying agents. The kaolin acts, in part, as an emulsifying agent to create an emulsion of cottonseed oil in water.

TABLE 5

| Treatments | Fresh weight of vegetation (g/m$^2$) |
| --- | --- |
| Untreated control | 710 |
| Kaolin + oil | 161 |
| Kaolin + oil + iron oxide | 132 |

These data indicate that the application of cottonseed oil emulsified with kaolin with/without iron oxide kills vegetation and the addition of iron oxide tends to enhance efficacy.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A method of reducing weed growth, comprising
applying to plant producing media hydrophobic particulate materials having a median individual particle size below about 100 µm to a depth of at least about 1 cm, wherein the plant producing media to the depth comprises about 1% by weight or more and about 25% by weight or less of the applied hydrophobic particulate materials.

2. The method of claim 1, wherein the hydrophobic particulate materials are applied to a depth of at least about 3 cm to about 30 cm.

3. The method of claim 1, wherein the plant producing media to the depth comprises about 2% by weight or more and about 15% by weight or less of the applied hydrophobic particulate materials.

4. The method of claim 1, wherein 90% by weight or more of the hydrophobic particulate materials have a particle size of less than about 3 microns.

5. The method of claim 1, wherein the hydrophobic particulate materials are applied by one of:

contacting a slurry comprising water, a salt, and the hydrophobic particulate materials with the plant producing media and mixing the slurry and the plant producing media;

applying the hydrophobic particulate materials in powder form to the plant producing media and mixing the hydrophobic particulate materials and the plant producing media; or mixing the hydrophobic particulate materials with loose plant producing media to form a mixture, applying the mixture to the plant producing media.

6. The method of claim 1, wherein the plant producing media comprises at least one selected from the group consisting of soil, peat, compost, vermiculite, and rockwool.

7. The method of claim 1, wherein the hydrophobic particulate materials comprise at least one selected from the group consisting of heat treated particulate materials, calcium carbonate, talc, kaolin, bentonites, pyrophyllite, silica, feldspar, sand, quartz, chalk, limestone, precipitated calcium carbonate, diatomaceous earth, barytes, aluminum trihydrate, pyrogenic silica, titanium dioxide, carbon soot, and coal dust.

8. The method of claim 1, wherein the hydrophobic particulate materials comprise a hydrophilic core and a hydrophobic outer surface.

9. A method of reducing weed growth, comprising
applying to plant producing media a mixture of particulate materials in agglomerate form having a median individual agglomerate size below about 500 µm and a high boiling organic liquid, and the particulate materials being selected from the group consisting of heat treated particulate materials, talc, kaolin, diatomaceous earth aluminum trihydrate, pyrogenic silica, titanium dioxide, carbon soot, and coal dust, wherein the particulate materials are applied to a depth of at least about 1 cm and the plant producing media to the depth comprises about 1% by weight or more and about 25% by weight or less of the applied particulate materials.

10. The method of claim 9, wherein the particulate materials in agglomerate form are applied to a depth of at least about 2 cm, wherein the plant producing media to the depth comprises about 2% by weight or more and about 15% by weight or less of the applied particulate materials.

11. The method of claim 9, wherein the mixture of particulate materials is applied by contacting the plant producing media with slurry comprising water and from about 5% by weight to about 50% by weight of the applied particulate materials.

12. The method of claim 11, wherein the high boiling organic liquid comprises at least one selected from the group consisting of oils and fatty acids.

13. The method of claim 9, wherein the particulate materials comprise hydrophobic particulate materials.

14. The method of claim 9, wherein the particulate materials comprise hydrous kaolin.

15. A method of reducing weed growth, comprising
applying to unwanted vegetation an emulsion comprising water, particulate materials having a median individual particle size below about 100 µm and a high boiling organic liquid selected from the group consisting of cottonseed oil, palm oil, peanut oil, corn oil, and soya oil to form a film, wherein the film has a thickness of about 5 µm or more and about 5 mm or less.

16. The method of claim 15, wherein 90% by weight or more of the particulate materials have a particle size of less than about 10 microns.

17. The method of claim 15, wherein the particulate materials comprise hydrous kaolin.

18. The method of claim 15, wherein the emulsion further comprises at least one selected from the group consisting of herbicides, pesticides, and fungicides.

19. The method of claim 15, wherein the particulate materials comprise at least one selected from the group consisting of calcium carbonate, talc, hydrous kaolin, calcined kaolin, bentonites, pyrophyllite, silica, feldspar, sand, quartz, chalk, limestone, precipitated calcium carbonate, diatomaceous earth and barytes, aluminum trihydrate, pyrogenic silica, titanium dioxide, carbon soot, and coal dust.

20. The method of claim 15, wherein the emulsion comprises cottonseed oil.

21. The unwanted vegetation having a film thereon according to claim 15.

22. A plot of land comprising
an upper layer beginning at the surface to a depth from about 3 cm to about 30 cm comprising soil and about 1% by weight or more and about 25% by weight or less of applied hydrophobic particulate materials having a median individual particle size below about 100 µm, wherein the particulate materials comprise one or more of beneficiated kaolin and heat treated particulate materials; and
a lower layer comprising at least one of soil, rocks, clay, and sand.

23. The plot of land of claim 22, wherein the upper layer comprises soil and about 2% by weight or more and about 15% by weight or less of applied calcined kaolin.

24. A method of reducing pests in and on plant producing media, comprising:
applying to plant producing media particulate materials having a median individual particle size below about 10 µm to a depth of at least about 1 µm, wherein the plant producing media to the depth comprises about 1% by weight or more and about 25% by weight or less of the applied particulate materials, and the particulate materials are selected from the group consisting of heat treated particulate materials, talc, kaolin, diatomaceous earth, aluminum trihydrate, pyrogenic silica, titanium dioxide, carbon soot, and coal dust.

25. The method of claim 24, wherein the particulate materials are applied to a depth of at least about 3 cm to about 30 cm.

26. The method of claim 24, wherein the particulate materials comprise hydrous kaolin and the pests comprise at least one selected from the group consisting of bacteria, fungus, worms, insects, arachnids, birds, rodents, deer, and rabbits.

27. The method of claim 24, wherein the particulate materials are applied to plant producing media in an emulsion, the emulsion comprising the particulate materials, water, and a high boiling organic liquid.

28. A method of enhancing horticultural effects of plants positioned in plant producing media, comprising
applying to the top surface of plant producing media particulate materials having a median individual particle size below about 10 µm to form a film having a thickness of about 1 µm or more and about 5 mm or less, the particulate materials having a Block Brightness of at least about 80.

29. The method of claim 28, wherein the particulate materials are applied to the top surface of plant producing media in an emulsion, the emulsion comprising the particulate materials, water, and a high boiling organic liquid.

30. A method of improving disease control of plants in plant producing media, comprising:
applying to plant producing media particulate materials having a median individual particle size below about 10 µm to a depth of at least about 3 cm, wherein the plant producing media to the depth comprises about 1% by weight or more and about 25% by weight or less of the applied particulate materials, and the particulate materials are selected from the group consisting of heat treated particulate materials, talc, kaolin, diatomaceous earth, aluminum trihydrate, pyrogenic silica, titanium dioxide, carbon soot, and coal dust.

31. The method of claim 30, wherein the particulate materials are applied to plant producing media in an emulsion, the emulsion comprising the particulate materials, water, and a high boiling organic liquid.

32. A method of increasing the size of fruit harvested from a fruit tree, comprising applying to the fruit tree having a first number of flowers an emulsion comprising water, particulate materials having a median individual particle size below about 100 µm and a high boiling organic liquid so that the fruit tree has a second number of flowers within about 2 weeks after the application, wherein the second number is at least about 25% less than the first number.

33. The method of claim 32, wherein the fruit tree is selected from the group consisting of apple trees, pear treas, peach trees, plum trees, lemon trees, grapefruit trees, avocado trees, orange trees, and apricot trees.

34. The method of claim 32, wherein the second number is at least about 50% less than the first number.

35. The method of claim 32, wherein the high boiling organic liquid comprises a high boiling organic liquid comprising from about 9 to about 20 carbon atoms.

36. The method of claim 32, wherein the particulate materials comprise at least one selected from the group consisting of calcium carbonate, talc, hydrous kaolin, calcined kaolin, bentonites, pyrophyllite, silica, feldspar, sand, quartz, chalk, limestone, precipitated calcium carbonate, diatomaceous earth and barytes, aluminum trihydrate, pyrogenic silica, titanium dioxide, carbon soot, and coal dust.

* * * * *

UNITED STATES PATENT AND TRADEMARK OFFICE
CERTIFICATE OF CORRECTION

PATENT NO. : 6,877,275 B2
DATED : April 12, 2005
INVENTOR(S) : Glenn et al.

It is certified that error appears in the above-identified patent and that said Letters Patent is hereby corrected as shown below:

<u>Title page,</u>
Item [73], Assignee, add -- The United States of America, as represented by the Secretary of Agriculture --.

Signed and Sealed this

Twenty-fifth Day of October, 2005

JON W. DUDAS
*Director of the United States Patent and Trademark Office*